US006263232B1

United States Patent
Norman, Jr.

(10) Patent No.: US 6,263,232 B1
(45) Date of Patent: Jul. 17, 2001

(54) METHOD AND KIT FOR LOCATING HYPERACTIVE PARATHYROID TISSUE OR ADENOMATOUS TISSUE IN A PATIENT AND FOR REMOVAL OF SUCH TISSUE

(75) Inventor: James G. Norman, Jr., Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/193,462

(22) Filed: Nov. 17, 1998

Related U.S. Application Data

(60) Provisional application No. 60/080,946, filed on Apr. 7, 1998.

(51) Int. Cl.⁷ .................................................. A61B 5/05
(52) U.S. Cl. ................................................................ 600/436
(58) Field of Search .................................... 600/407, 436

(56) References Cited

U.S. PATENT DOCUMENTS

| | | |
|---|---|---|
| 4,595,014 | 6/1986 | Barrett et al. . |
| 4,782,840 | 11/1988 | Martin, Jr. et al. . |
| 4,885,100 | 12/1989 | Iqbal et al. . |
| 5,008,418 | 4/1991 | Iqbal et al. . |
| 5,070,878 | 12/1991 | Denen . |
| 5,732,704 | 3/1998 | Thurston et al. . |

OTHER PUBLICATIONS

Arkles et al., Impact of complementary parathyroid scintigraphy and ultrasonography on the surgical management of hyperparathyroidism, *Surgery* 120(5): 845–851 (1996).
Attie, Surgical Treatment of Primary Hyperparathyroidism, 33–35.
Billy et al., Technetium–99m–Sestamibi Single Agent Localization Versus High Resolution Ultrasonography for the Preoperative Localization of Parathyroid Glands in Patients with Primary Hyperparathyroidism, *The American Surgeon* 61:882–888 (1995).
Borley et al., Technetium–99m sestamibi parathyroid localization is accurate enough for scan–directed unilateral neck exploration, *British Journal of Surgery* 83:989–991 (1996).
Caixas et al., Efficacy of preoperative diagnostic imaging localization of technetium 99m–sestamibi scintigraphy in hyperparathyroidism, *Surgery* 121(5):535–541 (1997).

(List continued on next page.)

*Primary Examiner*—William E. Kamm
(74) *Attorney, Agent, or Firm*—Howell & Haferkamp, L.C.

(57) ABSTRACT

Disclosed herein are methods for locating hyperactive parathyroid tissue in a patient. The methods comprise providing a radiopharmaceutical which produces during a time window after administration of the radiopharmaceutical to the patient, a detectably greater radioactivity in the hyperactive parathyroid tissue than in adjacent thyroid tissue in the patient; administering the radiopharmaceutical to the patient; surgically opening an operative field in the proximity of the hyperactive parathyroid tissue; and introducing into the operative field during the time window, a probe, which detects the radioactivity produced by the hyperactive parathyroid tissue to determine the location of the hyperactive parathyroid tissue upon moving the probe within the operative field. The method is particularly applicable to radioguided parathyroidectomy using a $^{99m}$Tc Sestamibi and a hand-held gamma detection probe. The gamma detection probe is also used to verify ex vivo that the resected tissue is parathyroid adenoma. Also provided are kits comprising a probe capable of detecting the radioactivity emitted from the hyperactive parathyroid tissue packaged with an instruction manual for use of the probe in performing a parathyroidectomy using $^{99m}$Tc Sestamibi.

37 Claims, 4 Drawing Sheets

OTHER PUBLICATIONS

Carter et al., Preoperative Detection of Sporadic Parathyroid Adenomas Using Technetium–99m–Sestamibi: What Role in Clinical Practice?, *The American Surgeon* 63:317–321 (1997).

Chapuis et al., Values of Ultrasonography, Sestamibi Scintigraphy, and Intraoperative Mesurement of 1–84 PTH for Unilateral Neck Exploration of Primary Hyperparathyroidism, *World J. Surg.* 20(7):835–840 (1996).

Denham et al., Cost–Effectiveness of Preoperative Sestamibi Scan for Primary Hyperparathyroidism is Dependent Solely upon the Surgeon's Choice of Operative Procedure, *J. Am. Coll. Surg.* 186(3):293–305 (1998).

Ditkoff et al., Parathyroid Surgery Using Monitored Anesthesia Care as an Alternative to General Anesthesia, *Amer.J. of Surg.* 172:698–700 (1996).

Hasselgren et al., Further Evidence Against the Routine Use of Parathyroid Ultrasonograph Prior to Initial Neck Exploration for Hyperparathyroidism, *Amer. J. of Surgery* 164:337–340 (1992).

Heller et al, Parathyroid Localization: Inability to Predict Multiple Gland Involvement, *Amer. J. of Surg.* 166:357–359 (1993).

Irvin et al., A New, Practical Intraoperative Parathyroid Hormone Assay, *Amer. J. of Surg.* 168:466–468 (1994).

Kotz, Advancing Medical Care: The role of Nuclear Medicine in Radioguided Surgery, *J. Nucl. Med.* 39:13N, 14N and 22N (1998).

Landry, Search for help finds USF pioneer, Tampa State, *The Times*, Oct. 15, 1998.

Light et al., Prospective Comparison of Dual–Phase Technetium–99m–Sestamibi Scintigraphy and High Resolution Ultrasonography in the Evaluation of Abnormal Parathyroid Glands, *The American Surgeon* 62: 562–568 (1996).

Lundgren et al., The Role of Preoperative Localization in Primary Hyperparathyroidism, *The American Surgeon* 61:393–396 (1995).

Malhotra et al., Preoperative Parathyroid Localization with Sestamibi, *American J. of Surgery* 172:637–640 (1996).

Martin et al., Evaluation of Single Isotope Technetium 99M–Sestamibi in Localization Efficiency for Hyperparathyroidism, *American J. of Surgery* 172:633–636 (1996).

McHenry et al., Parathyroid Localization with Technetium–99m–Sestamibi: A Prospective Evaluation, *J. American College of Surgeons*183:25–30 (1996).

Norman, et al., American Assoc. Endocrine Surgeons, Eighteenth Annual Meeting, p. 21, Apr. 6–8, 1997.

Norman, Minimally Invasive Radioguided Parathyroidectomy: An Endocrine Surgeon's Perspective, *J. Nucl. Med.* 39:15N and 24N (1998).

Norman, The Technique of Intraoperative Nuclear Mapping to Facilitate Minimally Invasive Parathyroidectomy, *Cancer Control* 4(6): 504 (1997).

O'Doherty et al., Parathyroid Imaging with Technetium–99–m–Sestamibi: Preoperative Localization and Tissue Uptake Studies, *J. of Nuclear Med.*33(3):313–318 (1992).

Robertson et al., Long–Term Results of Unilateral Neck Exploration for Preoperatively Localized Nonfamilial Parathyroid Adenomas, *Amer. J. of Surgery* 172:311–314 (1996).

Taillefer et al., Detection and Localization of Parathyroid Adenomas in Patients with Hyperparathyroidism Using a Single Radionuclide Imaging Procedure with Technetium–99m– Sestamibi (Double–Phase Study), *J. Nuclear Medicine* 33(10):1801–1807 (1992).

Thompson et al., Tumor–Associated Tissue Eosinophilia and Long–Term Prognosis for Carcinoma of the Larynx, *American J. of Surgery* 168:469–471 (1994).

Thompson et al., Parathyroid imaging with technetium–99m–sestamibi: An initial institutional experience, *Surgery* 116(6):966–973 (1994).

Wei et al., Analysis of Savings in Operative Time for Primary Hyperparathyroidism Using Localization with Technetium 99m Sestamibi Scan, *American J. of Surgery* 170:488–491 (1995).

Wei et al., Prospective evaluation of the efficacy of technetium 99m sestabibi and iodine 123 radionuclide imaging of abnormal parathyroid glands, *Surgery* 112(6):1111–1117 (1992).

METHOD AND KIT FOR LOCATING HYPERACTIVE PARATHYROID TISSUE OR ADENOMATIOUS TISSUE IN A PATIENT AND FOR REMOVAL OF SUCH TISSUE

RELATED APPLICATIONS

This application claims benefit to U.S. Provisional Application Serial No. 60/080,946 filed Apr. 7, 1998.

BACKGROUND OF THE INVENTION (1) Field of the Invention

This invention relates generally to the labeling and detecting of tissues using radionuclides and, more particularly, to the intraoperative mapping of hyperactive parathyroid tissues using a radiopharmaceutical and a hand-held detector and the application of such in a method for performing a parathyroidectomy.

(2) Description of the Related Art

Primary hyperparathyroidism results from a single parathyroid adenoma in 87–92 percent of all cases. Removal of this one gland produces a long-term cure. Nevertheless, most surgeons have performed a complete bilateral neck exploration in patients with primary hyperparathyroidism in order to examine and sometimes biopsy each gland in order to be certain that all hyperfunctional parathyroid tissues are found and resected, leaving behind only normal glands. This approach has been a consequence of the historical inability of preoperative testing to accurately distinguish those patients harboring a single diseased gland from the eight to thirteen percent of patients with multiple adenomas or four gland hyperplasia.

This began to change in the early 1990's following the discovery that $^{99m}$Tc Sestamibi, which had been used in cardiac imaging, preferentially concentrates in the parathyroid and can be used to localize parathyroid adenomas preoperatively (Taillefer et al., *J. Nucl Med* 33:1801–1807, 1992; Wei et al., *Surgery* 12:1111–1117, 1992). In the ensuing years, numerous surgeons have employed preoperative $^{99m}$Tc Sestamibi in gamma surface mapping to identify and locate parathyroid adenomas (Denham et al., *J Am Coll Surg* 186:293–304, 1998).

$^{99m}$Tc Sestamibi, which is a $^{99m}$Tc complex with 6 methoxy-isobutyl-isonitrile (see U.S. Pat. Nos. 4,885,100 and 5,008,418 assigned to E. I. duPont de Nemours and Company), is taken up by both hyperactive parathyroid tissue and adjacent thyroid tissue. Nevertheless, because of a more rapid rate of washout of this substance from the thyroid compared to the parathyroid, it has been possible to distinguish parathyroid from thyroid tissue by employing an early followed by a delayed surface mapping in the region of the parathyroid glands in single radionuclide, double-phase radioscintigraphy (Tailleferet al., supra; Wei et al., *Am J. Surg.* 170:488–491, 1995; O'Doherty et al., *J. Nucl. Med.* 33:313–318, 1992). These earlier approaches using dual-phase surface mapping perform an initial scan at about 15 to 20 minutes after intravenously injecting the $^{99m}$Tc Sestamibi followed by a delayed surface scan performed at anywhere from 90 minutes to 4 hours after injection (Billy et al., *Am Surgeon* 61:882–888, 1995; Yves et al., *World J. Surg.* 20:835–840, 1996; Carter et al., *Am. Surgeon* 63: 317–321; Martin et al., *Am. J. Surg.* 172:633–636, 1996; Caixas, et al., *Surgery* 121:53–541, 1997; Light et al., *Am. Surgeon* 62:562–568, 1996; Malhotra et al., *Am. J. Surg.* 172:63–64, 1996; McHenry et al., *J. Am. College Surgeons* 183:25–30, 1996). Although the use of dual-phase surface mapping constituted an advancement that improved the success rate of parathyroidectomy, nevertheless, not all parathyroid adenomas could be detected with a surface scan, particularly in multiglandular disease, such that bilateral neck dissection was still considered necessary for all parathyroidectomies (Martin et al., *Am J Surgery* 172:633–636, 1996).

At the same time that pre-operative dual-phase surface scanning was advancing parathyroidectomy methods, new hand-held imaging probes were being developed which allowed surgeons to identify radiolabeled cancers intraoperatively (see for example, U.S. Pat. Nos. 4,595,014 and 5,070,878). These probes were used to intraoperatively identify neoplasms and sentinel lymph nodes which could then be surgically removed (see U.S. Pat. Nos. 4,782,840 and 5,732,704). The use of such hand-held imaging probes during the operative procedure proved to be more effective in identifying neoplasms than surface mapping in that the hand-held intraoperative probe was often able to locate neoplasms that were not detected by the surface mapping (for example, see U.S. Pat. No. 4,782,840).

Recently, intraoperative mapping with a gamma probe has been used to facilitate the performance of parathyroidectomies (Norman et al., *Am. Assoc. Endocrine Surgeons, Eighteenth Annual Meeting*, page 21, Apr. 6–8, 1997). This early approach performed the surgery 3±0.1 hours after $Tc^{99}$ Sestamibi surface mapping, which would be expected to be about 3 hours and 15 minutes after injection of the radiopharmaceutical. Nevertheless, this early reported method would not be effective in identifying parathyroid adenomas because this report did not consider any possible interfering effect of adjacent thyroid tissue, which could limit the effective time during which any meaningful intraoperative mapping could be performed. Furthermore, the prior experience with pre-operative surface scanning would have provided no insight as to whether there would even be any interfering effect of adjacent thyroid tissue during intraoperative mapping because surface scanning would detect much less radioactivity than that measured deep in the neck at the site of a parathyroid adenoma and thyroid gland. This is due to the inverse square rule whereby the radioactivity significantly declines at increasing distances from the source. Indeed, as noted above, preoperative surface mapping was known to be a poor predictor of the presence of neoplasms, which were often not identified by the surface mapping, but found using an intraoperative probe. (see U.S. Pat. No. 4,782,840). In addition, as also noted above, surface mapping was known to sometimes fail to identify adenomas, whereas, as discussed below, 100% of adenomas can be identified using the intraoperative method disclosed herein. Thus, one would not have been able to predict whether thyroid tissue would interfere with detecting adjacent parathyroid adenomas and, if so, whether there would be a time window for performing intraoperative mapping of parathyroid adenomas.

Although other methods for localizing parathyroid adenomas have been studied such as the use of double-isotope surface mapping techniques, ultrasonography and intraoperative measurement of hormonal levels, these approaches have also proved to be less than completely effective in identifying all parathyroid adenomas (see for example, Keith et al., *Am J. Surg.* 166:357–359, 1993; Martin et al., *Am J. Surg.* 172:633–636, 1996; Chapuis et al., *World J. Surg.* 20:835–840, 1996;). Thus, there remains a continuing need to develop more effective methods for identifying parathyroid adenomas.

BRIEF DESCRIPTION OF THE INVENTION

Accordingly, the inventor herein has succeeded in discovering that during a particular time window after administration of a radiopharmaceutical, intraoperative mapping of radioactivity using a hand-held probe can localize hyperactive parathyroid tissue that accumulates the radiopharmaceutical to permit differentiation of the hyperactive parathyroid tissue from adjacent tissues and resection of the diseased tissue in a parathyroidectomy procedure. Thus, the present invention involves a method for locating hyperactive parathyroid tissue in a patient. The method comprises providing a radiopharmaceutical which produces during a time window after administration of the radiopharmaceutical to the patient, a detectably greater radioactivity in the hyperactive parathyroid tissue than in adjacent thyroid tissue in the patient. In one aspect of the invention, the radiopharmaceutical can be selected on the basis of its capability of producing a detectably greater radioactivity in the hyperactive parathyroid tissue with respect to adjacent thyroid tissue during the time window. The radiopharmaceutical is administered to the patient and an operative field is surgically opened in the proximity of the hyperactive parathyroid tissue. A probe capable of detecting the radiation emitted from the radiopharmaceutical is then introduced into the operative field during the time window to detect the radioactivity localized to the hyperactive parathyroid tissue and determine the location of the hyperactive parathyroid tissue upon moving the probe within the operative field. Thus, the time window characteristic of the radiopharmaceutical dictates the time during which the probe is introduced into the operative field as well as the time during which the surgery is performed.

Preferably, the radiopharmaceutical is a gamma-emitting radiopharmaceutical and the probe detects the gamma radiation emitted from the hyperactive parathyroid tissue. The radiopharmaceutical may comprise $^{99m}$Tc and, in particular, $^{99m}$Tc Sestamibi in the amount of about 15 to about 25 mCi, more preferably, about 20 mCi of the $^{99m}$Tc Sestamibi is used in the method. The method can be used to detect parathyroid adenomas.

In a significant aspect of the present invention, the gamma probe is introduced into the operative field during a time window of between about 1.5 and about 3 hours after injecting the radiopharmaceutical and more preferably at about 2.5 hours.

The present invention also provides, in another aspect of this embodiment, a method for performing a parathyroidectomy to remove hyperactive parathyroid tissue. The method comprises locating the hyperactive parathyroid tissue according to the method of this embodiment and excising the hyperactive parathyroid tissue. In another aspect of the present invention, the parathyroidectomy can also involve the performance of preoperative surface mapping of radioactivity performed initially at about 15 minutes and, subsequently, at a delayed time no greater than 90 after injecting the radiopharmaceutical. It is also contemplated within the scope of the present invention, that a first injection of the radiopharmaceutical can be performed followed by surface mapping and a second injection of the radiopharmaceutical can be performed followed by performing the surgery during the time window after the second injection.

One particularly advantageous aspect of the invention is the use of the probe to ascertain whether the tissue resected from the patient is, in fact, hyperactive parathyroid tissue. Thus, after removal of tissue, the probe is used to detect radioactivity in the tissue. Tissue showing at least 20% of the level of radioactivity remaining in the operative field from which the tissue was removed is deemed to be the hyperactive parathyroid tissue.

In a further embodiment, the present invention provides another method for locating hyperactive parathyroid tissue in a patient. The method comprises selecting a time window during which the hyperactive parathyroid tissue has detectably greater radioactivity than adjacent thyroid tissue in the patient following administration of a gamma-emitting radiopharmaceutical. The radiopharmaceutical is administered to the patient and an operative field is surgically opened in the proximity of the hyperactive parathyroid tissue. A probe capable of detecting the radiation emitted from the radiopharmaceutical is then introduced into the operative field during the time window to detect the radioactivity emitted from the hyperactive parathyroid tissue and determine the location of the hyperactive parathyroid tissue upon moving the probe within the operative field. Thus, the time window characteristic of the radiopharmaceutical dictates the time during which the probe is introduced into the operative field as well as the time during which the surgery is performed.

Preferably, the radiopharmaceutical is a gamma-emitting radiopharmaceutical and the probe detects the gamma radiation emitted from the hyperactive parathyroid tissue. The radiopharmaceutical preferably comprises $^{99m}$Tc and, in particular, $^{99m}$Tc Sestamibi in the amount of about 15 to about 25 mCi. More preferably, about 20 mCi of the $^{99m}$Tc Sestamibi is used. The method is preferably used to detect parathyroid adenomas.

In a significant aspect of this embodiment of the present invention, the gamma probe is introduced into the operative field during a time window of between about 1.5 and about 3 hours after the injecting the radiopharmaceutical and more preferably at about 2.5 hours.

The present invention also provides, in a variation of this embodiment, a method for performing a parathyroidectomy to remove hyperactive parathyroid tissue. The method comprises locating the hyperactive parathyroid tissue according to the method of this embodiment and excising the hyperactive parathyroid tissue. In another aspect of the present invention, the parathyroidectomy can also involve the performance of preoperative surface mapping of radioactivity performed initially at about 15 minutes and, subsequently, at a delayed time no greater than 90 after injecting the radiopharmaceutical. It is also contemplated within the scope of the present invention, that a first injection of the radiopharmaceutical can be performed followed by surface mapping and a second injection of the radiopharmaceutical can be performed followed by performing the surgery during the time window after the second injection.

In another aspect, this embodiment can also provide a method to ascertain whether the tissue resected from the patient is, in fact, hyperactive parathyroid tissue. After removal of tissue, the probe is used to detect radioactivity in the tissue. Tissue showing at least 20% of the level of radioactivity remaining in the operative field from which the tissue was removed is deemed to be the hyperactive parathyroid tissue.

In still another embodiment, the present invention provides a kit for use in performing a parathyroidectomy. The kit comprises a probe capable of detecting a radiopharmaceutical, and in particular, a gamma-emitting radiopharmaceutical, packaged with a manual providing instructions for use of the probe to locate hyperactive parathyroid tissue in a radioguided surgical procedure. Preferably, the probe identifies parathyroid adenomas. The instructions provide that following administration of a radiopharmaceutical which produces a detectably greater radioactivity in the hyperactive parathyroid tissue than adjacent thyroid tissue, the probe is to be introduced into an operative field surgically opened in the proximity of the hyperactive parathyroid tissue to detect the radioactivity emitted from the hyperactive parathyroid tissue. Preferably, the radiopharmaceutical comprises a gamma-emitting radiopharmaceutical, more preferably, $^{99m}$Tc, and, in particular, $^{99m}$Tc Sestamibi in an amount of 15 to 25 mCi and, more preferably, about 20 mCi.

In a significant aspect, this embodiment can in some instances provide further instructions for introducing the gamma probe into the operative field during a time window in which the gamma-emitting radiopharmaceutical produces a detectably greater radioactivity in the hyperactive parathyroid tissue than adjacent thyroid tissue. Preferably, the manual specifies a time window for introducing the probe into the operative field between about 1.5 and about 3 hours after the injection of the radiopharmaceutical and more preferably at about 2.5 hours.

In another aspect, the manual can provide instructions to ascertain whether the tissue resected from the patient is, in fact, hyperactive parathyroid tissue. After removal of tissue, the probe is used to detect radioactivity in the tissue and tissue showing at least 20% of the level of radioactivity remaining in the operative field from which the tissue was removed is deemed to be the hyperactive parathyroid tissue.

In still another embodiment, the present invention provides a method for distinguishing an adenoma from adjacent non-adenomatous tissue in a re-operative surgical field in a patient that has previously undergone surgical intervention in the same field. The method comprises administering to the patient a radiopharmaceutical, which produces a detectably greater radioactivity in the adenoma than in adjacent non-adenomatous tissue in the patient followed by surgically opening the re-operative field. A probe capable of detecting the radiopharmaceutical is introduced into the re-operative field to detect the radioactivity emitted from the adenoma and determine the location of the adenoma upon moving the gamma probe within the re-operative field. Preferably, the radiopharmaceutical is a gamma-emitting radiopharmaceutical and the method distinguishes a parathyroid adenoma from adjacent thyroid tissue based upon the radiopharmaceutical producing a detectably greater radioactivity in the parathyroid adenoma than in adjacent thyroid tissue in the patient.

In a significant aspect of this embodiment, the gamma-emitting radiopharmaceutical used to detect parathyroid adenomas can produce a detectably greater radioactivity in the parathyroid adenoma than in adjacent thyroid tissue in the patient during a time window. This time window dictates the time during which the gamma probe is introduced into the re-operative field and the time for performing the surgery as well.

Preferably, the radiopharmaceutical comprises $^{99m}$Tc and, in particular, $^{99m}$Tc Sestamibi in the amount of about 15 to about 25 mCi. More preferably, about 20 mCi of the $^{99m}$Tc Sestamibi is used. The method is, preferably, used to detect parathyroid adenomas.

In a significant aspect of this embodiment of the present invention, the gamma probe is introduced into the re-operative field during a time window of between about 1.5 and about 3 hours after injecting the radiopharmaceutical and more preferably at about 2.5 hours.

The present invention also provides, in a variation of this embodiment, a method for performing a parathyroidectomy to remove hyperactive parathyroid tissue, the method comprising locating the hyperactive parathyroid tissue according to the method of this embodiment and excising the hyperactive parathyroid tissue. In another aspect of the present invention, the parathyroidectomy can also involve the performance of preoperative surface mapping of radioactivity performed at about 15 minutes and/or at about 90 or less after injecting the radiopharmaceutical. It is also contemplated within the scope of the present invention, that a first injection of the radiopharmaceutical can be performed followed by surface mapping and a second injection of the radiopharmaceutical can be performed followed by performing the surgery during the time window after the second injection.

In another aspect, this embodiment can also provide a method to ascertain whether the tissue resected from the patient is, in fact, hyperactive parathyroid tissue. After removal of tissue from the re-operative field, the probe is used to detect radioactivity in the tissue. Tissue showing at least 20% of the level of radioactivity remaining in the operative field from which the tissue was removed is deemed to be the hyperactive parathyroid tissue.

In yet another embodiment, the present invention provides a kit for use in performing a parathyroidectomy. The kit comprises a probe capable of detecting a radiopharmaceutical, and in particular, a gamma-emitting radiopharmaceutical. The kit further includes a manual providing instructions for use of the probe to locate hyperactive parathyroid tissue in a radioguided surgical procedure. Preferably, the probe identifies parathyroid adenomas. The instructions provide that following administration of a radiopharmaceutical which produces a detectably greater radioactivity in the hyperactive parathyroid tissue than adjacent thyroid tissue, the probe is to be introduced into a re-operative field surgically opened in the proximity of the hyperactive parathyroid tissue to detect the radioactivity produced by the hyperactive parathyroid tissue. Preferably, the radiopharmaceutical comprises a gamma-emitting radiopharmaceutical, more preferably the radiopharmaceutical comprises $^{99m}$Tc, and, even more preferably, $^{99m}$Tc Sestamibi in an amount of 15 to 25 mCi and, preferable, about 20 mCi.

In a significant aspect, this embodiment can, in some instances, provide further instructions for introducing the gamma probe into the re-operative field during a time window in which the gamma-emitting radiopharmaceutical produces a detectably greater radioactivity in the hyperactive parathyroid tissue than adjacent thyroid tissue. Preferably, the manual specifies a time window for introducing the probe into the re-operative field between about 1.5 and about 3 hours after the injection of the radiopharmaceutical and more preferably at 2.5 hours.

In another aspect, the manual can provide instructions to ascertain whether the tissue resected from the patient is, in fact, hyperactive parathyroid tissue. After removal of tissue from the re-operative field, the probe is used to detect radioactivity in the tissue. Excised tissue showing at least 20% of the level of radioactivity remaining in the re-operative field from which the tissue was removed is deemed to be the hyperactive parathyroid tissue.

The present invention also provides, in another embodiment, a method for locating an ectopic parathyroid adenoma positioned in the chest of a patient, from adjacent non-adenomatous tissue. The method comprises administering to the patient a radiopharmaceutical which produces a detectably greater radioactivity in the parathyroid adenoma than in the adjacent non-adenomatous tissue in the patient. An operative field is surgically opened in the proximity of the parathyroid adenoma via an incision between two ribs or through the bed of a resected rib segment of the patient and a probe, adapted for insertion into the operative field and capable of detecting the radioactivity emitted from the radiopharmaceutical in the parathyroid adenoma, is introduced into the operative field to detect the radioactivity localized to the parathyroid adenoma and determine the location of the parathyroid adenoma upon movement of the gamma probe within the operative field. The method preferably employs optical scopes in conjunction with the probe.

Preferably, the radiopharmaceutical is a gamma-emitting radiopharmaceutical and the probe detects the gamma radiation emitted from the hyperactive parathyroid tissue. The radiopharmaceutical preferably comprises $^{99m}Tc$, more preferably, $^{99m}Tc$ Sestamibi in the amount of about 15 to about 25 mCi. More preferably, about 20 mCi of the $^{99m}Tc$ Sestamibi is used. The method is, preferably, used to detect parathyroid adenomas.

In a significant aspect of this embodiment of the present invention, the gamma probe is introduced into the operative field during a time window of between about 1.5 and about 3 hours after the injecting the radiopharmaceutical and more preferably at about 2.5 hours.

In a variation of this embodiment, the present invention also provides for performing a parathyroidectomy to remove hyperactive parathyroid tissue. The method comprises locating the hyperactive parathyroid tissue according to the method of this embodiment and excising the hyperactive parathyroid tissue. In another aspect of the present invention, the parathyroidectomy can also involve the performance of preoperative surface mapping of radioactivity performed at about 15 minutes and/or at about 90 or less after injecting the radiopharmaceutical. It is also contemplated within the scope of the present invention, that a first injection of the radiopharmaceutical can be performed followed by surface mapping and a second injection of the radiopharmaceutical can be performed followed by performing the surgery during the time window after the second injection.

In another aspect, the method can provide for ascertaining whether the tissue resected from the patient is, in fact, hyperactive parathyroid tissue. After removal of tissue from the operative field, the probe is used to detect radioactivity in the tissue. Excised tissue showing at least 20% of the level of radioactivity remaining in the operative field from which the tissue was removed is deemed to be the hyperactive parathyroid tissue.

Among the several advantages achieved by the present invention, therefore, may be noted the provision of new methods for locating hyperactive thyroid tissue and kits for performing the methods; the provision of new parathyroidectomy methods which are minimally invasive, requiring only a small incision under local anesthesia; the provision of new parathyroidectomy methods which can be performed in a short period of time on an outpatient basis; the provision of new methods for performing parathyroidectomies wherein the success rate for removal of the diseased tissue is approximately 100%; the provision of a new method for verifying the identity of tissue excised during a parathyroidectomy in which the method can be performed in the operative room at the time of surgery or, alternatively, in the pathology laboratory; the provision of an new and effective method for performing a parathyroidectomy in a re-operative surgical field in a patient that has previously undergone surgical intervention in the same field; and the provision of an effective new method for performing a parathyroidectomy in a patient with ectopic hyperactive parathyroid tissue.

DETAILED DESCRIPTION OF THE INVENTION

Figure 1:
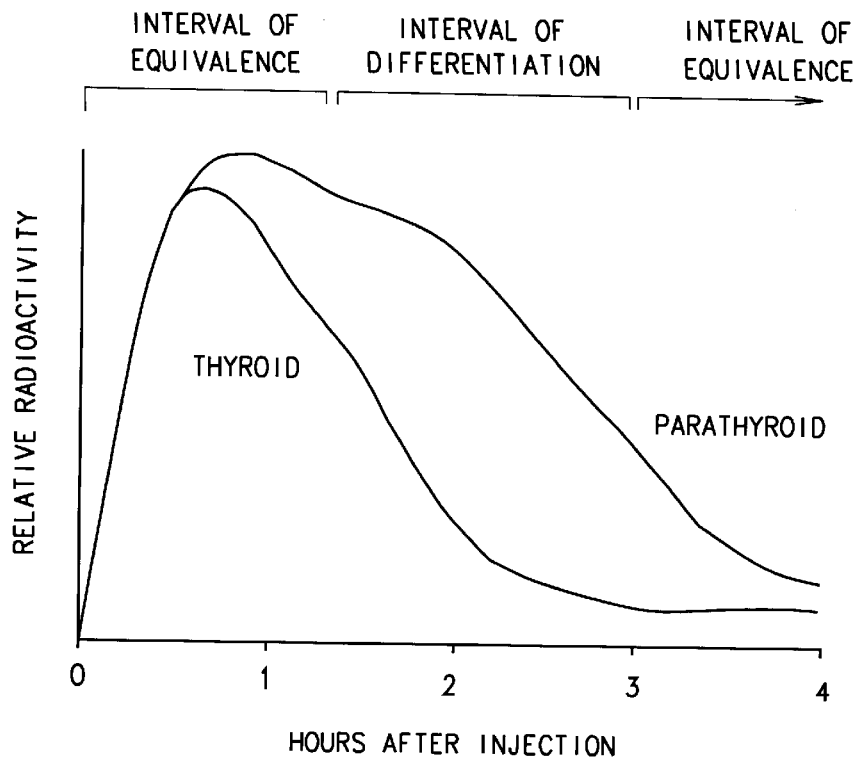
FIG. 1 illustrates the time course of radioactivity in 75 patients, each having a single parathyroid adenoma, following intravenous injection of $^{99m}Tc$ Sestamibi, measured in counts/sec intraoperatively using one or more hand-held gamma probe of 10, 11, 12 or 14 mm at the site of either the parathyroid adenoma or the adjacent thyroid tissue in which the values are calculated relative to the radioactivity from the heart measured over the chest.

In accordance with the present invention, it has been discovered that intraoperative radiation mapping using a hand-held probe can localize a hyperactive parathyroid tissue containing a radiopharmaceutical and significantly facilitate the performance of a parathyroidectomy procedure when the mapping is performed during a particular time window after administration of the radiopharmaceutical to the patient. During this time window, the amount of radioactivity detected from hyperactive parathyroid tissue is distinguishable greater than that measured in adjacent thyroid tissue.

The radiopharmaceutical for use in the invention comprises a radionuclide in a compound that produces a detectable concentration in the hyperactive parathyroid tissue to allow its detection during the mapping procedure. One consideration, therefore, is the half-life of the radionuclide portion of the radiopharmaceutical. The radionuclide preferably has a half-life greater than 90 minutes so that mapping and surgical resection of the hyperactive parathyroid tissue can be performed during the same procedure, but less than 10 days so that the patient is not exposed to radiation for an extended period. Radioactive isotopes such as the technetium isotope, $^{99m}$Tc, which has a half-life of 6 hours, or the thallium isotope, $^{201}$Tl, which has a half-life of 74 hours, or the indium isotope $^{113m}$In, which has a half-life of 99.8 minutes, have been used in patients in medical therapy and in diagnosis and have suitable half-lifes for use in the present invention. In addition, isotopes having half-lifes longer than 10 days can also be use provided that the biological half life for elimination of the radiolabeled pharmaceutical from the patient is not greater than 10 days. It is preferably that the isotope used produces gamma emissions as do $^{99m}$Tc or $^{201}$Tl or $^{113m}$In, and that the gamma emission produced by the isotope be detectable by the hand-held probe. Nevertheless, it is contemplated within the scope of the present invention that isotopes producing beta emissions such as $^{42}$K or $^{24}$Na can, alternatively, be used along with a hand-held probe suitable for detecting beta radiation. The radioisotope can be incorporated into and used in the form of a radiopharmaceutical compound. For example, $^{201}$Tl is often used in the form of thallous chloride and $^{99m}$Tc is often used in the form of [$^{99m}$Tc]pertechnate or technetium-99m-methoxyisobutylisonitrile, i.e., $^{99m}$Tc Sestamibi (see, for example, O'Doherty et al., *J Nucl. Med.* 33:313–318, 1992).

The radiopharmaceutical for use in the present invention is selected on the basis of its preferentially concentrating in hyperactive parathyroid tissue compared to adjacent tissue over the time period of intraoperative mapping. The particular characteristics of the radiopharmaceutical which allow the hyperactive parathyroid tissue to be distinguished from adjacent thyroid tissue are the kinetics of uptake and washout of the radiopharmaceutical from the parathyroid tissue and thyroid tissues. Thus, it is important that the radiopharmaceutical be initially taken up by the hyperactive parathyroid tissue, preferably, to a greater extent than by the adjacent thyroid tissue and/or that the radiopharmaceutical be lost by the thyroid tissue after its initial uptake at a faster rate than by the hyperactive parathyroid tissue. This differential washout, which is preferably coupled with a differential initial uptake of the radiopharmaceutical, produces a time window during which hyperactive parathyroid tissue emits greater radioactivity than the adjacent thyroid tissue and, as a result, the hyperactive parathyroid tissue can be distinguished from thyroid tissue. The skilled artisan can readily determine the suitability of a given radionuclide for use in the present method by, for example, assessing the ability of the radiopharmaceutical to concentrate in parathyroid and thyroid tissues as well as the time window for distinguishing between the tissues using animal and tissue models known in the art.

When using $^{99m}$Tc Sestamibi as the radionuclide, the hyperactive parathyroid tissue produces surprisingly greater radioactivity that can be detected by a hand-held gamma detector than that produced by adjacent thyroid tissue during a period of from about 1.5 hours to about 3 hours after intravenous injection. It had been reported in a prior publication that parathyroidectomy surgery facilitated by intraoperative nuclear mapping could be performed 3±0.1 hours after $^{99m}$Tc Sestamibi scanning (Norman et al, *Am. Assoc. Endocrine Surgeons Annual Meeting* 1997, p. 21, Apr. 6–8, 1997). Three hours after an initial scan would be expected to be about 3 hours and 15 minutes after injection of the $^{99m}$Tc Sestamibi. However, the count rate is not high enough at three hours after injecting the $^{99m}$Tc Sestamibi and thereafter, to permit the surgeon to adequately distinguish the hyperactive parathyroid tissue (see Kotz, *J Nucl Med.* 39:13N–22N, 1998). For this reason, radioguided parathyroidectomies using intraoperative nuclear mapping cannot be performed in most patients at 3 hours and 15 minutes after injection of $^{99m}$Tc Sestamibi. Indeed, as has been discovered and reported herein, the time window for performing intraoperative nuclear mapping to identify hyperactive parathyroid tissue is preferably between 1.5 hours and 3 hours after injecting $^{99m}$Tc Sestamibi and more preferably between 2 and 2.5 hours after injecting $^{99m}$Tc Sestamibi.

The amount of radiolabeled pharmaceutical that is administered to the patient is such that at least about 100 to 400 counts per second difference can be detected between the hyperactive parathyroid tissue and adjacent thyroid tissue although this varies with dosage, time after injection, size of the patient, depth of the hyperactive parathyroid tissue, and the size/manufacturer of the probe. Preferable, the patient is injected intravenously with from about 15 to about 25 mCi of radiopharmaceutical and more preferably, about 20 mCi of radiopharmaceutical. The term "about" as used herein is intended to reference a range of values between 10% less than and 10% greater than the indicated value. Thus, about 20 mCi is intended to mean the range of values from 18 to 22 mCi.

The probe can preferably be characterized by having a collimatable and shielded radiation detector with a selective photon entrance for example, as described in U.S. Pat. Nos. 4,595,014, 4,782,840, 5,070,878 and 5,732,704. Probes useful in the method of the present invention are, preferably, from about 7 to about 14 mm in size. Studies reported herein used an 11-mm hand-held gamma probe, such as that commercially available from Neoprobe Corp., Dublin Ohio and probes ranging in size from 8 to 14 mm from U.S. Surgical Corporation, Norwalk, Conn. and Ethicon Surgical. Larger, non-shielded probes such as those that have been available in the past do not provide the sensitivity necessary to distinguish background radioactivity of the thyroid gland from the more radioactive but adjacent hyperactive parathyroid tissue. These large probes can work well for lymphatic mapping and sentinel node identification because there is little or no background radioactivity. However, the first generation of hand-held probes are not applicable to parathyroidectomy surgery because they are too large to be inserted into a small neck wound. Furthermore and, more importantly, the early probes are not columnated or shielded enough to allow differentiation between the hyperactive parathyroid tissue and adjacent thyroid tissue. Thus, the new smaller, columnated and shielded probes are preferred for use in radioguided parathyroidectomy surgery.

The probe is endowed with some read-out method to indicate the level of radioactivity such as by visual display operably coupled to the probe or, preferably, by producing an audible sound response which can be manifested, for example, in the form of a siren. The preferred audible response provides an indicia of the number of output pulses counted and provides the surgeon with a readily perceptible signal as the probe window is moved across the boundary of the hyperactive parathyroid tissue and adjacent, less radioactive tissue to thus identify the boundaries of the hyperactive tissue. This guides the surgeon without detracting from his ability to resect diseased tissue along the boundaries identified by the probe.

Figure 6:
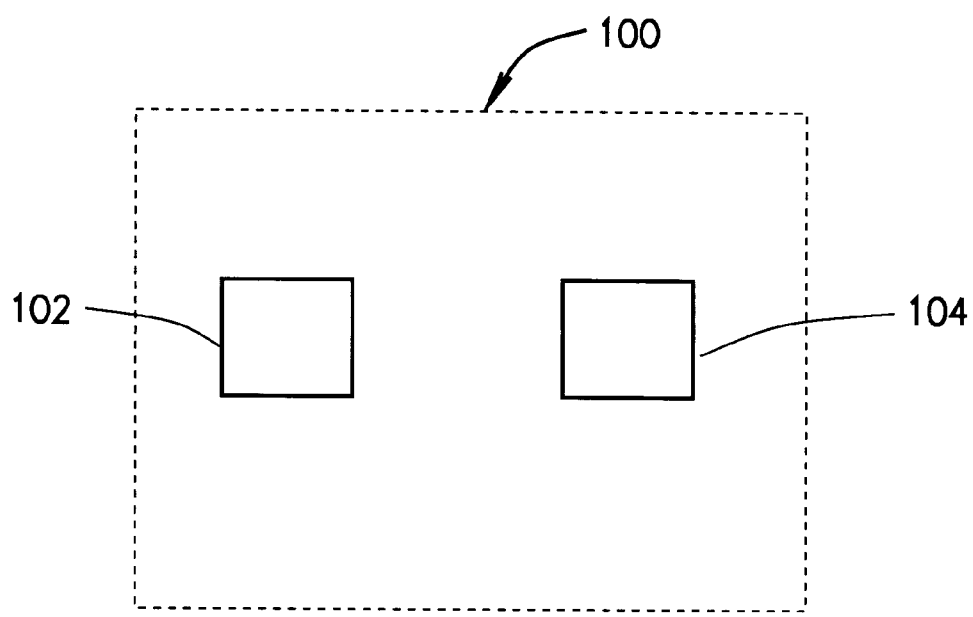
FIG. 6 is a schematic drawing of a kit of the present invention having a probe capable of detecting radioactivity packaged with a manual providing instructions for use of the probe for locating hyperactive parathyroid tissue following administration of a radiopharmaceutical.

The probe for use in the present invention can be supplied in a kit which includes a manual providing instructions for use of the probe in the methods of the present invention. Referring to FIG. 6, the kit is generally indicated by reference numeral 100. The probe is generally indicated at 102 and the manual is generally indicated at 104. The manual indicates that the probe can be used for locating hyperactive parathyroid tissue following administration of a radiopharmaceutical which produces a detectably greater radioactivity in the hyperactive parathyroid tissue than adjacent thyroid tissue, by introducing into a surgically opened operative field in the proximity of the hyperactive parathyroid tissue the probe which detects the radioactivity produced by the hyperactive parathyroid tissue. The manual can be in any medium suitable for conveying instructions including, for example, a booklet providing written instructions, an audio and/or video tape providing written, audible or visual instructions, a CD rom providing written, audible or visual instructions, a package insert providing reference to literature articles that detail the method of the present invention or any other medium conveying instructions for performing the method of the present invention.

The method of the present invention can localize hyperactive parathyroid tissues of different types. In the case of $^{99m}$Tc Sestamibi, accumulation of the radiopharmaceutical occurs in mitochondria in a manner dependent upon the aerobic metabolism of the tissues. As a result, the radiopharmaceutical tends to concentrate in tissue with a high level of aerobic metabolism. For this reason, normal parathyroid tissue is not very effective in accumulating the $^{99m}$Tc Sestamibi, especially during the clinical situation discussed herein where normal parathyroid glands will behave appropriately to a high serum calcium concentration becoming metabolically dormant. On the other hand, hyperactive parathyroid tissues are metabolically more active which results in accumulation of the $^{99m}$Tc Sestamibi. This, in turn, results in a high level of radioactivity being emitted from the hyperactive parathyroid tissue which allows the tissue to be localized by the method of this invention. Hyperactive parathyroid tissues that are particularly applicable for detection and localization by this method include parathyroid adenomas, hyperplastic parathyroid tissues and parathyroid cancers. In particular, the method utilizing $^{99m}$Tc Sestamibi is effective in identifying and localizing parathyroid adenomas.

The method of localizing hyperactive parathyroid tissue is applicable to the performance of parathyroidectomy procedures. Previous parathyroidectomy procedures were aided by external pre-operative gamma surface mapping and such can be advantageously used in conjunction with the intraoperative mapping of the present invention. Thus, an initial surface scan can be performed approximately 15 minutes after injecting the radiopharmaceutical, $^{99m}$Tc Sestamibi. A delayed scan can also be performed, however, it is preferable to perform this second scan at about 60 to 90 minutes instead of 2 to 3 hours as has been previously done.

The surgery is performed during the time window such that the hand-held gamma probe can be used to identify hyperactive parathyroid tissue and guide the surgery. Prior to the surgery, the patient is anesthetized using a general anesthetic or, preferably, using a local anesthetic such as lidocaine and epinephrine coupled with intravenous sedation according to procedures known in the art. A surgical field is then opened in the general region of the hyperactive parathyroid tissue. Preferably, this involves initially placing a 2.0 cm incision in the expected location of the hyperactive parathyroid tissue followed by creating subplatysmal flaps 1 to 2 cm in all directions. The dissection is then carried deeper as directed by the gamma probe and the hyperactive parathyroid tissue is identified an excised. The surgery can in some instance be facilitated by the use optical scopes to aid in visualization of tissues showing radioactivity as the probe is moved through the operative field as well as to aid in resecting the tissues once identified.

In addition to the applicability of the present method for identifying hyperactive parathyroid tissue in the operative field of the patient's neck, the method can also be applied in another aspect of the invention to ex vivo examination of tissue excised by measuring the radioactivity emitted from the excised tissue. This can verify to the surgeon that the tissue resected is, in fact, hyperactive parathyroid tissue. The ex vivo measuring of radioactivity of the excised tissue can advantageously be performed during the surgical procedure such that pathological identification of the tissue using frozen sections is not necessary. The measurement of ex vivo radioactivity in resected hyperactive parathyroid tissues is based upon the observation by the inventor herein that resected hyperactive parathyroid tissue emits a level of radiation which is at least 20% and occasionally more than 100% that of post excision background radiation measured in the area of the neck form which the excised tissue was taken. The mean value was 62% of background radioactivity in the neck. The background radiation in the neck exceeds the radiation emitted from the resected tissue even though the $^{99m}$Tc Sestamibi was concentrated in the resected tissue because of the greater mass of tissue in the neck. By way of comparison, ex vivo fat and lymph node tissue show less than 10% of background, having a mean value of about 2.5% of background emissions in the neck. Thus, tissue resected from the neck can be verified as being hyperactive parathyroid tissue by measuring the radioactivity of the excised tissue, measuring the background radioactivity in the neck in the region from which the tissue was removed and determining whether the radioactivity of the ex vivo tissue exceeds that of the background region in the neck. If the radioactivity emitted by the tissue exceeds 20% of background, it is deemed to be hyperactive parathyroid. Conversely, if the excised tissue produces less than 20% of the radioactivity measured as background levels in the neck, then the tissue is not hyperactive parathyroid tissue. In the performance of over 200 parathyroidectomies by the procedure of the present invention to date, the success rate for removal of single gland parathyroid adenomas has been 100%.

In another aspect of the present invention, the methods herein can be used to facilitate the performance of re-operative surgical procedures. Re-operative explorations of the neck for persistent and recurrent hyperparathyroidism are typically difficult operations which carry a higher complication rate than first time operations. This is because the growth reparative tissues into the prior surgical field tends to obliterate otherwise recognizable anatomical structures and landmarks. The method of the present invention can advantageously provide a new approach to such re-operative procedures by providing a means to identify the boundaries between hyperactive parathyroid tissue and adjacent non-diseased tissue. Accordingly, the method of radioguided identification of hyperactive tissue can be used in re-surgeries in which there is a complete absence of visual landmarks to identify the boundaries of hyperactive parathyroid tissues. The method is performed in the same manner as for first time surgeries except that no visual cues are used to locate the hyperactive parathyroid tissue. Such re-surgeries are nearly 100% effective in identifying and excising hyperactive parathyroid tissues in patients having a single adenoma.

The present methods are also applicable to intraoperative mapping of ectopic hyperactive parathyroid tissue. In particular, the present method has been utilized in identifying and removing ectopic glands located in the anterior mediastinum. The method involves an approach through chest wall in which the operative field is opened via an incision between two ribs or through the bed of a resected rib segment of the patient. The surgery then proceeds deeper into the region of the hyperactive parathyroid tissue using the hand-held gamma probe to guide the dissection. The surgery can, in some instances, be facilitated by using optical scopes to aid in visualization of tissues showing radioactivity as the probe is advanced through the operative field as well as to aid in resecting the tissues once identified.

Preferred embodiments of the invention are described in the following examples. Other embodiments within the scope of the claims herein will be apparent to one skilled in the art form consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the identification of the time window for localizing hyperactive parathyroid tissue using a hand-held gamma probe following intravenous injection of $^{99m}$Tc Sestamibi.

Data from seventy-five patients was compiled for identification of the time window for differentiating hyperactive parathyroid tissue from adjacent thyroid tissue. The patients all had single parathyroid adenoma as identified in preoperative surface mapping as well as by intraoperative examination of the four quadrants of the neck. Each patient received an intravenous injection of a dose of from about 15 to about 25 mCi $^{99m}$Tc Sestamibi, depending upon the patients weight, and an initial surface scan was performed about 15 minutes after injection. This was followed by a delayed scan performed just prior to surgery about 60 to about 90 minutes after intravenous injection. The surgical field was opened via an initial incision of about 2 cm. The wound was then extended by deeper dissection of the tissue into the region of the parathyroid tissue. An 11-mm handheld Neoprobe gamma detector (Neoprobe Corp. Dublin, Ohio) or a 10, 11, 12 or 14 mm probe from U.S. Surgical was used to guide the dissection and to intraoperatively map the tissues for radioactivity.

In order to characterize the window during which the parathyroid can be distinguished from the adjacent thyroid tissue, the probe was placed at the site of either the hyperactive parathyroid tissue or the thyroid tissue and the counts/sec measured. In each patient, the measurements of radioactivity in the parathyroid and thyroid tissues were normalized by comparing to the radioactivity measured from the heart which effectively concentrates the $^{99m}$Sestamibi. To do this, the probe was placed over the chest of the patient and radioactivity emitted from the heart measured. This was then used as a standardizing reference amount of radioactivity for each patient. The ratio of counts/sec measured in either the hyperactive parathyroid tissue or in the thyroid tissue were normalized by dividing by counts/sec measured over the heart to obtain relative radioactivity values. Values of relative radioactivity for parathyroid tissue and thyroid tissue were determined at various times from about 60 minutes after injection of the $^{99m}$Tc Sestamibi to about 4 hours after injection. The results are reported in FIG. 1.

As can be seen in the figure, the parathyroid tissue exhibited higher radioactivity levels than the thyroid from about 60 minutes to 4 hours after injection of the $^{99m}$Tc Sestamibi. During an initial period of from 0 to about 1.5 hours (labeled in the figure as "Interval of Equivalence"), both the parathyroid and thyroid emit a high level of radioactivity such that the two tissues cannot be distinguished intraoperatively during surgery. Beginning about 1.5 hours and lasting until about 3 hours after injection, the radioactivity measured in the hyperactive parathyroid tissue is substantially greater than that of the thyroid, thus providing a time window during which the radioguided surgery can be performed. This period is labeled in FIG. 1 as the "Interval of Differentiation". After 3 hours, the amount of radioactivity detectable in the hyperactive parathyroid tissue rapidly declined to levels that were too low to provide any meaningful assistance to the surgeon in localizing and identifying the boundaries of the parathyroid tissue. This is identified in FIG. 1 as another "Interval of Equivalence". Thus, the results of this study indicates that radioguided parathyroidectomy surgery using $^{99m}$Tc Sestamibi must be performed between about 1.5 hours and 3 hours after injection of the $^{99m}$Tc Sestamibi.

EXAMPLE 2

This example illustrates the application of the method of the invention to the performance of parathyroidectomies in patients.

The protocol for performing radioguided parathyroidectomies has been reported in the literature (Norman, Cancer Control 4:500–504, 1997) and the inventor herein has now used this method in over 200 cases. The method as reported in the first set of 15 patients is as follows.

Figure 2:
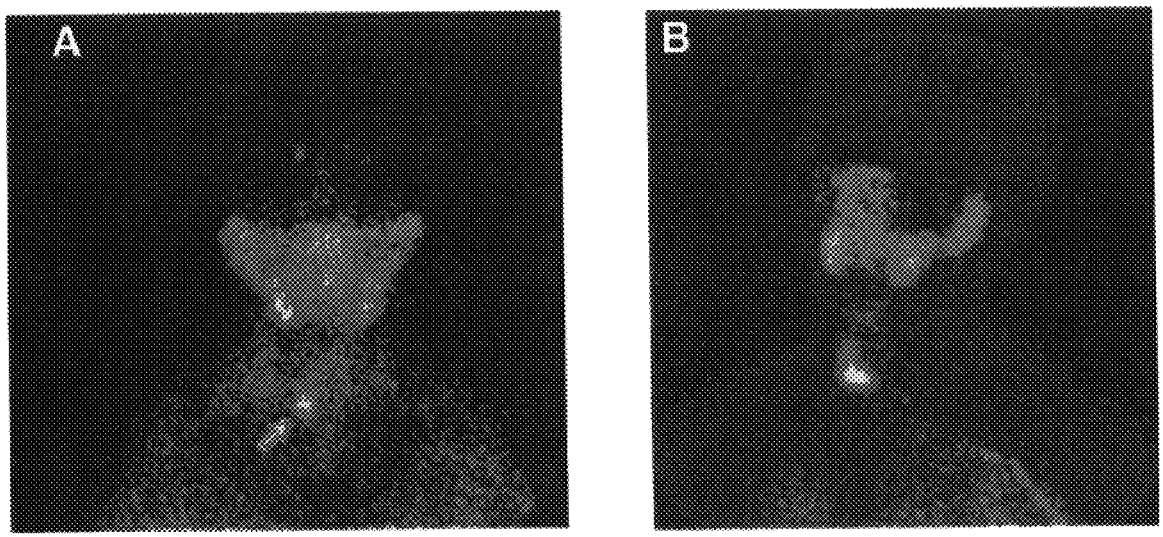
FIG. 2 illustrates two delayed anterior view Sestamibi surface scans demonstrating (A) a true-positive surface scan that was verified to be a single adenoma using the gamma probe and (B) a false-positive surface scan which was determined to be a large hyperplastic gland with the probe.

Fifteen consecutive patients with biochemical evidence of primary hyperparathyroidism in whom a high quality Sestamibi scan demonstrated a single adenoma were entered into a prospective study of minimally invasive unilateral neck exploration identify and remove a single adenoma. Patients were scanned immediately after intravenous injection of a dose of from 15 to 25 mCi $^{99m}$Tc Sestamibi, the particular dose depending upon the patient's weight. This was followed by a delayed scan performed 2.5±0.1 hours after the initial scan and immediately prior to surgery. FIG. 2 illustrates typical delayed surface scans. Panel A shows a true-positive scan which identified an adenoma that was verified intraoperatively and panel B shows a false-positive scan that was intraoperatively found to be a large hyperplastic gland.

After the patient was positioned on the operating room table, a suitable hand-held gamma probe was used to measure radioactivity in four quadrants of the neck, defined by the upper and lower poles of the thyroid gland on each side. By protocol, an initial 2.0 cm incision was placed according to the expected location of the adenoma as determined by both Sestamibi scanning and measurement of gamma emissions with the probe. The incision was occasionally higher or lower than usual, but all were oriented transversely to allow extension as needed for even conversion to bilateral exploration if necessary. Subplatysmal flaps were created 2 to 3 cm in all directions, and radioactivity was quantitated again for all four quadrants. The dissection was carried deeper as directed by increasing gamma emissions to locate the radioactive gland. If the gamma emissions equilibrated in all four quadrants once the targeted gland was removed, no attempt was made to identify a normal ipsilateral gland and the wound was closed. If no such equilibration was noted, further dissection was performed to identify the remaining radioactive source. Ex vivo radioactivity was determined for resected parathyroid gland and for adipose tissue (n=14), and lymph nodes (n=10).

Anesthetic technique varied. The first five procedures were performed with the patient under general endotracheal anesthesia. Once experience was gained with the minimal approach, all subsequence resections were performed with a local anesthetic (lidocaine, 1% with epinephrine) and intravenous sedation (propofol). The timing of hospital discharge was not determined by protocol but rather according to surgeon preference, taking into account patient age and associated medical conditions, anesthetic technique, and time of day. All cases were monitored for the time required to find the adenoma, total operative time (incision to skin closure), length of incision, and duration of hospital stay.

Figure 3:
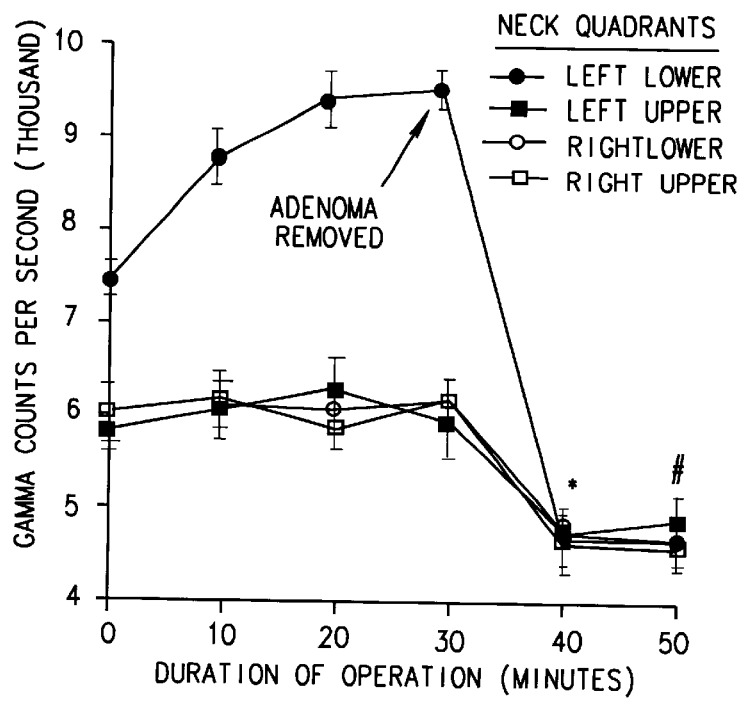
FIG. 3 illustrates the counts/sec (±SEM) measured in mapping neck radioactivity during resection of left lower adenomas in which gamma emissions from four neck quadrants were obtained from five patients before making skin incision (time 0) followed by subsequent gamma measurements at 10 minute intervals showing initial high level of gamma counts in lower left quadrant which decreased ($p<0.0001$) to a level not significantly different from that in the other three quadrants and showing that radioactivity in all quadrants decreased to new lower levels ($p<0.05$) upon removal of adenomas.

Radioactivity was monitored in the operating room by direct counting with a Geiger counter and through the wearing of radiation-detection devices by the operating surgeon. Radioactive emissions were determined for the specimen, surgeon's gloves and gown, patient drapes, and soiled sponges. Comparisons of repeated observations were by analysis of variance, whereas pooled data were compared by the unpaired Student's t test. Calculations were performed with statistical software (epistat, Richardson, Tex.). Nuclear mapping before the skin incision showed a single quadrant of the neck that emitted gamma radiation significantly higher than the other three quadrants, which correlated with the Sestamibi scan (FIG. 3, time zero). Once the subplatysmal flaps were created, the radioactivity in the targeted quadrant increased, whereas the others did not. Adenomas were located by this technique in 14 patients in an average of 19±1.7 minutes. Removal of the adenoma resulted in a rapid loss of neck radioactivity in that quadrant ($p<0.0001$; FIG. 3), whereas the remainder of the neck demonstrated in a significant decline in background radioactivity ($p<0.05$). The new baseline radioactivity was equal for all four quadrants of the neck (difference not significant) after successful resection of an adenoma.

Figure 4:
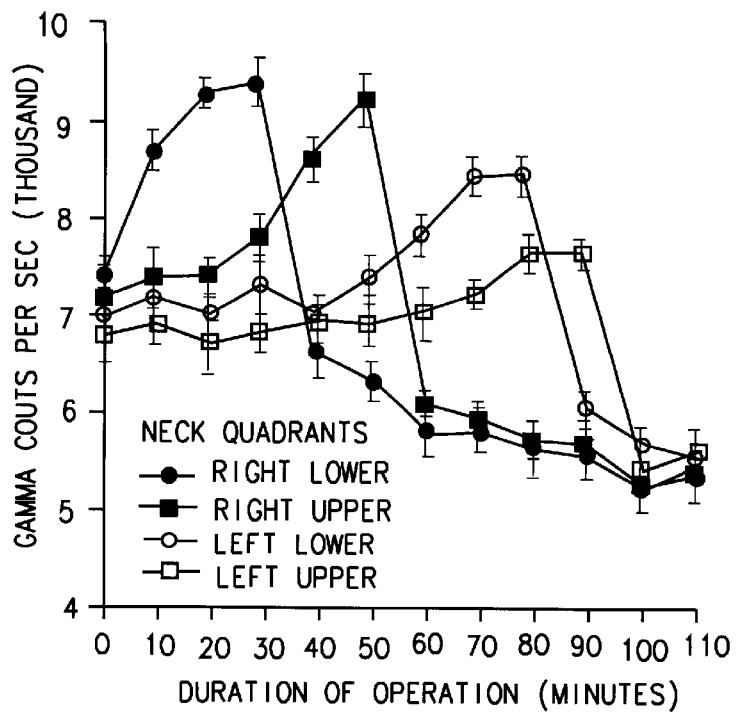
FIG. 4 illustrates the counts/sec (±SEM) measured in mapping neck radioactivity during resection of four-gland hyperplasia in which preoperative surface mapping suggested a single source of radioactivity in the lower right quadrant but removal of a large abnormal parathyroid gland found in the quadrant failed to significantly lower neck radioactivity or equalize the radioactivity in all quadrants until further radioguided dissection resulted in discovery and resection of three other hyperplastic glands.

A single patient failed to demonstrate a new lower baseline radioactivity and equalization of emissions from all four quadrants after the removal of the targeted enlarged gland. Further exploration guided by the gamma probe revealed another enlarged gland on the ipsilateral side (FIG. 4), which then prompted a bilateral exploration. Four gland hyperplasia was subsequently diagnosed and an autotransplantation was performed in the sternocleidomastoid muscle. All patients had normal serum calcium and parathyroid hormone levels after operation.

Although all incisions were initially 2.0 cm in length, seven (47%) were extended to facilitate safe removal of the adenoma (average 2.4±0.2 cm), and one was extended to 4.5 cm to allow for bilateral neck exploration in the patient with four gland hyperplasia. The average operative time for resection of an adenoma was 48±2.1 minutes.

Both anesthetic technique and hospital stay were modified during the study. The first five minimally invasive operations were performed with the patient under general anesthesia, and four patients were kept overnight for observation (23-hour admission). As experience with this technique was gained, local anesthetics became routine, with the last 10 being performed by this technique. Similarly, all patients in whom procedures were performed with local anesthetics (and one performed under general anesthesia) were discharged the same day with 3.0 hours of operation (average, 2.4±0.2 hours).

Figure 5:
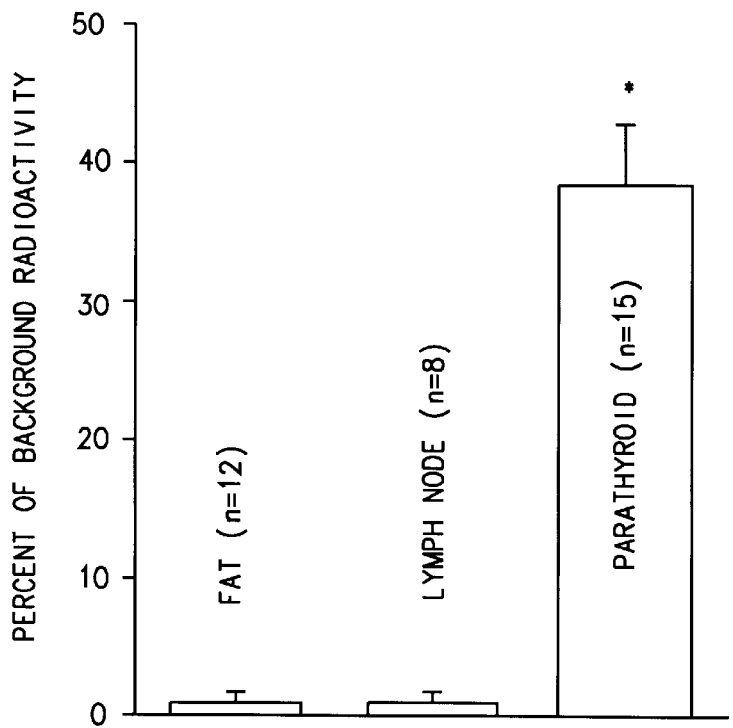
FIG. 5 illustrates the ex vivo gamma emissions from parathyroid adenomas excised from patients during parathyroidectomy procedures compared to low level gamma emissions measured from fat and lymph nodes also excised from the patients.

Ex vivo radioactivity proved to be 100% accurate in distinguishing parathyroid tissue from fat and lymph nodes (FIG. 5). All adenomas emitted radiation at a level at least 20% of background neck emissions (mean, 32%±4.3%), whereas the emissions from fat and lymph nodes never exceeded 3% of neck emissions (mean, 1.8%±0.2%; $p<0.0001$).

Monitoring of operating room radioactivity demonstrated no apparent radioactive hazard. The surgeon was potentially exposed to the highest concentrations of radioactivity; however, monitors worn on a finger and the anterior part of the chest demonstrated minimal exposure (0.05 rem 15 cases), which is not deemed to be a significant risk. Similarly, there was no detectable increase in radioactivity over background on used surgical drapes or sponges containing patients' blood (difference not significant). All parathyroid tissue emitted gamma radiation that correlated somewhat with the size of the adenoma but never exceeded twice background radiation (mean, 0.06±0.01 mR/hr).

A number of recent publications have advocated unilateral neck exploration for patients with primary hyperparathyroidism in whom a preoperative Sestamibi scan demonstrates a single adenoma as the offending gland. The failure of this technique to gain wide acceptance, however, can be related to many surgeons' experience with this and other localizing studies that were of poor quality or failed to add significant information that would allow for a minimal exploration with confidence. It is the reproducibility of results that has been the main obstacle to date, because any number of studies can accurately identify a single adenoma at least some of the time. In contrast to the vast majority of published reports examining the accuracy of Sestamibi scanning before the initial neck exploration, the present method takes advantage of the very high specificity this test offers and selected for minimal exploration only those patients identified as having single-gland disease on delayed images. This selective approach allows the surgeon to avoid the false-negative test results afforded by the 85% to 94% sensitivity of Sestamibi and perform only a minimal exploration on those with a high quality scan showing a single adenoma. The main concern, therefore, becomes elimination of the few false-positive scans that would suggest that a patient has a single adenoma when multiple adenomas or hyperplasia is present. This is addressed by using intraoperative nuclear mapping several hours after injection of the radiopharmaceutical at a time when parathyroid tissue has the greatest differential activity compared with surrounding structures. The gamma probe was able to detect a hot spot on the skin confirming the location of an adenoma, as suggested on the just completed Sestamibi scan in 12 of 15 patients. The patient subsequently found to have four-gland hyperplasia and another two with a solitary adenoma deep in the posterior mediasteinum showed equal emissions at the skin level in all four quadrants. Once the subplatysmal plane was developed, however, increased radioactivity became apparent in one neck quadrant in all patients. Below the platysma the probe was used frequently to direct the dissection in three dimensions because counts increase as the probe gets closer to the source of radioactivity. Once identified, the adenoma is removed by blunt dissection of surrounding structures and placement of a single mini-hemoclip on its pedicle. The recurrent laryngeal nerve is examined as it pertains to the operative field at hand. It is important to use blunt dissection almost exclusively and bipolar electrocautery only when necessary.

Several considerations allow the identification of the tissue excised as the adenoma. First, the excised adenoma emits radioactivity at least 20% and occasionally higher than 100% of post-excision background (typical ex vivo emissions around 1500 counts/sec). Fat, lymph nodes, and even thyroid nodules will never show this level of radioactivity (typical ex vivo emissions around 110 counts/sec). This should reduce the number of "diagnostic" frozen sections because it becomes readily apparent what type of tissue has been removed. With removal of the radioactive gland, gamma emissions within that quadrant of the neck decrease dramatically. The loss of this main focus of radioactivity within the neck will also cause the establishment of a new background level of radioactivity in all quadrants of the neck and most important, the radioactivity in all four quadrants will equalize. Failure of any of these expected observations to be manifest suggests that another hyperfunctional gland is present that contains more $^{99m}$Tc-labeled Sestamibi than surrounding tissues. This is a direct result of the greater sensitivity of the gamma probe placed within the tissues of the neck than the gamma camera used for routine Sestamibi scanning. The approach to this situation is to use the probe to direct the subsequent dissection. Conversely, the ipsilateral gland can be identified and examined histologically.

An important aspect of this operative technique is that the dissection is directed by radioactivity rather than the surgeon's expectation of the location of the offending gland. This allows for incisions as small as 2.0 cm because they can be placed in a position overlying the radioactive gland. Preferably, all incisions are made transversely so they can be extended as necessary. The use of the probe also allows the resection to be performed rather quickly. Adenomas were identified an average of 19 minutes after incision of the skin (range, 11 to 47 minutes). One patient had a completely intrathyroidal parathyroid gland that was found within 24 minutes. Its hidden position was disclosed by a decline in radioactivity behind the thyroid gland and the demonstration of emissions several thousand per second higher in one specific portion of the thyroid gland compared with the remainder of the gland. Although the speed at which an operation is performed is not important in itself. These times are a reflection of a simplicity of this technique.

In an additional patient, the method was successfully applied to identifying and removing an ectopic parathyroid which had migrated from the neck to the chest. For this patient, a probe longer than the 11 mm gamma probe was used. The probe was of a length suitable for accessing the region of the gland through the chest wall from the underarm region. The adenoma was successfully removed through an incision of about 2 cm. Access to such ectopic parathyroid adenomas can be via an incision between ribs or through a resected portion of a rib. In addition, more time may be required for such surgery to remove an ectopic parathyroid and if this exceeds the time window of three hours, a second injection of $^{99m}$Tc Sestamibi can be given.

Detailed monitoring of the potential radiation hazards has shown this procedure to pose no significant risk to operating room personnel, surgeon, or pathologist. The surgeon's exposure is relatively insignificant, and the cumulative radiation dose acquired with 15 cases is 1% of acceptable yearly exposure (5 rem) as determined by the Nuclear Regulatory Commission. Similarly, the radioactive adenoma sent to the pathology laboratory contains only slightly more radioactivity than does the background (0.04 mR/hr) and therefore poses no exposure hazard to frozen section personnel and does not contaminate the cryostat or other instruments or liquids. The soiled linens and sponges do not require special handling and can be discarded as routine. Cumulative data have recently been reviewed the State of Florida Office of Radiation Control, and they concur with the conclusions herein.

When selected appropriately, most patients with primary hyperparathyroidism may be treated successfully through a minimally invasive technique. The use of a local anesthetic and the limited scope of the dissection afforded by intraoperative nuclear mapping may decrease the incidence of failed explorations and other potential complications associated with this operation for all but the most experienced endocrine surgeons. A high quality Sestamibi scan is essential for the success of this approach and is facilitated greatly by interaction between the nuclear radiologist and the surgeon.

EXAMPLE 3

This example illustrates the application of the method of the invention in re-surgery procedures to treat persistent and recurrent primary hyperparathyroidism.

Re-operative explorations of the neck for persistent and recurrent hyperparathyroidism are typically difficult operations which carry a higher complication rate than first time operations. Although surgeons attempt to identify the hyperactive gland prior to re-exploration, general anesthesia and several hours of operating room time are still required. Recent experience with over 100 radioguided minimally invasive parathyroidectomies has shown dramatic benefits to patent, surgeon, and hospital provided by the small operative field, local anesthesia, 35 minute operative time, and same day discharge. This experience has led us to examine the technique of radioguided minimal parathyroidectomy for patents with persistent or recurrent primary hyperparathyroidism.

Fifteen patients underwent exploration for persistent (13) or recurrent (2) disease during a 14 month period. All patients had a previous bilateral neck exploration and three had an ipsilateral thyroid lobectomy as well. Prior to re-exploration, all patients underwent Sestamibi scanning which correctly identified a solitary adenoma in 14 (93% sensitivity, 100% specificity). The use of intraoperative nuclear mapping (radioguided parathyroidectomy) was determined by surgeon preference or the unavailability of the probe and not by the location of the tumor (with the exception of one not demonstrated on Sestamibi).

All patents were cured without complications. The results are shown in the table below.

| Exploration Type | Number | Local anesthesia | Operative Times | Incision Length | Out Patient | 23 Hour Stay | 1–3 Day Stay |
|---|---|---|---|---|---|---|---|
| Radio-guided | 11 | 9* (82%) | 48* (Range 17–109) | 3.5 cm * | 7* (64%) | 4 (36%) | 0 |
| Standard | 4 | 0 | 151 min. (Range 118–177) | 9.5 cm | 0 | 2 (50%) | 2 (50%) |

*$P < 0.05$

Thus, re-operative parathyroid surgery can be made dramatically easier for the surgeon and patient alike when full advantage is taken of the radioactivity which concentrates in most adenomas. A high quality Sestamibi will demonstrate the majority of these tumors, but the operation must be conducted within 3 hours of isotope injection for the probe to detect differences between the adenoma and background radioactivity. This technique allows for a much small operation (non-standard incision and/or approach to the gland) which is directed by radioactivity rather than anatomical structures and landmarks which are usually absent or unrecognizable in the re-operative neck.

All references cited in this specification are hereby incorporated by reference. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results attained.

As various changes could be made in the above methods and compositions without department from the scope of the invention, it is intended that all matter contained in the above description and shown in the accompanying drawings shall be interpreted as illustrative and not in a limiting sense.

What is claimed is:

1. A method for performing a parathyroidectomy in a patient to remove a parathyroid adenoma, the method comprising: intravenously injecting $^{99m}$Tc Sestamibi into the patient; surgically opening an operative field in the proximity of the parathyroid adenoma; introducing into the operative field during a time window of from 2 to 2.5 hours after administering the $^{99m}$Tc Sestamibi, a gamma-detecting probe to determine the location of the parathyroid adenoma upon moving the probe within the operative field; and excising tissue identified as parathyroid adenoma.

2. A method according to claim 1 further comprising verifying that the excised tissue is parathyroid adenoma by determining the radioactivity of the excised tissue wherein excised tissue having radioactivity of 20% or greater than radioactivity measured in the operative field after excision of the tissue is deemed to be parathyroid adenoma.

3. A method for performing a parathyroidectomy in a patient to remove a parathyroid adenoma, the method comprising: intravenously injecting $^{99m}$Tc Sestamibi into the patient; selecting a time window of from about 1.5 to about 3.0 hours after injecting the $^{99m}$Tc Sestamibi; surgically opening an operative field in the proximity of the hyperactive parathyroid tissue during the time window; introducing into the operative field during the time window, a gamma-detecting probe to determine the location of parathyroid adenoma upon moving the probe within the operative field; and excising tissue identified as parathyroid adenoma.

4. A method according to claim 3 further comprising verifying that the excised tissue is hyperactive parathyroid tissue by determining the radioactivity of the excised tissue wherein excised tissue having radioactivity of 20% or greater than radioactivity measured in the operative field after excision of the tissue is deemed to parathyroid adenoma.

5. A method for locating hyperactive parathyroid tissue in a patient, the method comprising: providing a radiopharmaceutical which produces during a time window after administration of the radiopharmaceutical to the patient, a detectably greater radioactivity in the hyperactive parathyroid tissue than in adjacent thyroid tissue in the patient; administering the radiopharmaceutical to the patient; surgically opening an operative field in the proximity of the hyperactive parathyroid tissue; and introducing into the operative field during the time window, a probe, which detects the radioactivity localized to the hyperactive parathyroid tissue to determine the location of the hyperactive parathyroid tissue upon moving the probe within the operative field.

6. A method according to claim 5 wherein the hyperactive parathyroid tissue comprises a parathyroid adenoma, wherein the step of providing a radiopharmaceutical comprises providing a radiopharmaceutical which produces during a time window after administration of the radiopharmaceutical to the patient a detectably greater radioactivity in the parathyroid adenoma, and wherein the step of surgically opening the operative field comprises surgically opening an operative field in the proximity of the parathyroid adenoma.

7. A method according to claim 6 wherein the providing of the radiopharmaceutical comprises providing a gamma emitting radiopharmaceutical, and wherein the introducing of the probe comprises introducing into the operative field a gamma-detecting probe.

8. A method according to claim 7 wherein administering the radiopharmaceutical comprises administering a radiopharmaceutical comprising $^{99m}$Tc.

9. A method according to claim 8 wherein administering the radiopharmaceutical comprising $^{99m}$Tc. comprises administering a radiopharmaceutical comprising $^{99m}$Tc Sestamibi.

10. A method according to claim 9 wherein the introducing of the gamma probe into the operative field comprises introducing the gamma probe into the operative field during a time window of between about 1.5 and about 3 hours after the injecting the radiopharmaceutical.

11. A method according to claim 9 wherein the introducing of the gamma probe into the operative field comprises introducing the gamma probe into the operative field about 2.5 hours after injecting the radiopharmaceutical.

12. A method for performing a parathyroidectomy to remove hyperactive parathyroid tissue comprising locating the hyperactive parathyroid tissue according to the method of claim 5 and excising the hyperactive parathyroid tissue.

13. A method according to claim 12 wherein the method further comprises verifying that the excised tissue is hyperactive parathyroid tissue by determining the radioactivity of the excised tissue wherein excised tissue having radioactivity of 20% or greater than radioactivity measured in the operative field after excision of the tissue is deemed to be hyperactive parathyroid tissue.

14. A method according to claim 12 wherein the method further comprises verifying that the excised tissue is hyperactive parathyroid tissue by determining the radioactivity of the excised tissue wherein excised tissue having radioactivity of 20% or greater than radioactivity measured in the operative field after excision of the tissue is deemed to be a parathyroid adenoma.

15. A method according to claim 12 wherein the step of administering the radiopharmaceutical to the patient constitutes administering a second dose of the radiopharmaceutical to the patient, the method further comprising administering a first dose of the radiopharmaceutical to the patient; and performing a gamma surface mapping using a gamma detection device after the first dose of the radiopharmaceutical is administered to the patient, the gamma surface mapping occurring before the second dose of the radiopharmaceutical is administered to the patient.

16. A method for locating hyperactive parathyroid tissue in a patient comprising: selecting a time window during which the hyperactive parathyroid tissue has detectably greater radioactivity than adjacent thyroid tissue in the patient following administration of a radiopharmaceutical; administering the radiopharmaceutical to the patient; surgically opening an operative field in the proximity of the hyperactive parathyroid tissue; and introducing into the operative field during the time window, a probe which detects the radioactivity localized in the hyperactive parathyroid tissue to determine the location of hyperactive parathyroid tissue upon moving the probe within the operative field.

17. A method according to claim 16 wherein the administration of a radiopharmaceutical comprises administration of a gamma-emitting radiopharmaceutical and wherein the introducing of the probe into the operative field comprises introducing a gamma-detecting probe into the operative field.

18. A method according to claim 16 wherein the locating of hyperactive parathyroid tissue comprises locating a parathyroid adenoma.

19. A method according to claim 18 wherein administering the radiopharmaceutical comprises administering a radiopharmaceutical comprising $^{99m}$Tc.

20. A method according to claim 19 wherein administering the radiopharmaceutical comprising $^{99m}$Tc comprises administering a radiopharmaceutical comprising $^{99m}$Tc Sestamibi.

21. A method according to claim 20 wherein the introducing of the gamma probe into the operative field comprises introducing the gamma probe into the operative field during a time window of between about 1.5 and about 3 hours after injecting the radiopharmaceutical.

22. A method according to claim 20 wherein the introducing of the gamma probe into the operative field comprises introducing the gamma probe into the operative field about 2.5 hours after injecting the radiopharmaceutical.

23. A method for performing a parathyroidectomy to remove hyperactive parathyroid tissue comprising locating the hyperactive parathyroid tissue according to the method of claim 16 and excising the hyperactive parathyroid tissue.

24. A method according to claim 23 further comprising verifying that the excised tissue is hyperactive parathyroid tissue by determining the radioactivity of the excised tissue wherein excised tissue having radioactivity of 20% or greater than radioactivity measured in the operative field after excision of the tissue is deemed to be hyperactive parathyroid tissue.

25. A method for performing a parathyroidectomy to remove a parathyroid adenoma comprising locating the parathyroid adenoma according to the method of claim 16 and excising the parathyroid adenoma.

26. A method according to claim 25 wherein the step of administering the radiopharmaceutical to the patient constitutes administering a second dose of the radiopharmaceutical to the patient, the method further comprising administering a first dose of the radiopharmaceutical to the patient, and performing a gamma surface mapping using a gamma detection device after the first dose of the radiopharmaceutical is administered to the patient, the gamma surface mapping occurring before the second dose of the radiopharmaceutical is administered to the patient.

27. A kit comprising a probe capable of detecting radioactivity packaged with a manual providing instructions for use of the probe for locating hyperactive parathyroid tissue following administration of a radiopharmaceutical which produces a detectably greater radioactivity in the hyperactive parathyroid tissue than adjacent thyroid tissue, by introducing into a surgically opened operative field in the proximity of the hyperactive parathyroid tissue the probe which detects the radioactivity produced by the hyperactive parathyroid tissue.

28. A method for distinguishing an adenoma from adjacent non-adenomatous tissue in a re-operative surgical field, the method comprising: administering to the patient a radiopharmaceutical which produces a detectably greater radioactivity in the adenoma than in adjacent non-adenomatous tissue in the patient; surgically opening the re-operative field and introducing into the re-operative field a gamma probe to detect the radioactivity produced by the adenoma and determine the location of the adenoma upon moving the gamma probe within the re-operative field.

29. A method for locating a parathyroid adenoma positioned in the chest of a patient, from adjacent non-adenomatous tissue, the method comprising: administering to the patient a radiopharmaceutical which produces a detectably greater radioactivity in the parathyroid adenoma than in the adjacent non-adenomatous tissue in the patient; surgically opening an operative field in the proximity of the parathyroid adenoma via an incision between two ribs or through the bed of a resected rib segment of the patient; and introducing into the operative field a probe adapted for insertion into the operative field wherein the probe detects the radioactivity produced by the parathyroid adenoma top determine the location of the parathyroid adenoma upon movement of the probe within the operative field.

30. A method according to claim 29 wherein the providing of the radiopharmaceutical comprises providing a gamma-emitting radiopharmaceutical and wherein the introducing of the probe comprises introducing into the operative field a gamma-detecting probe.

31. A method according to claim 30 wherein administering the radiopharmaceutical comprises administering a radiopharmaceutical comprising $^{99m}$Tc.

32. A method according to claim 31 wherein administering the radiopharmaceutical comprising $^{99m}$Tc. comprises administering a radiopharmaceutical comprising $^{99m}$Tc Sestamibi.

33. A method according to claim 32 wherein the introducing of the gamma probe into the operative field comprises introducing the gamma probe into the operative field during a time window of between about 1.5 and about 3 hours after the injecting the radiopharmaceutical.

34. A method according to claim 32 wherein the introducing of the gamma probe into the operative field comprises introducing the gamma probe into the operative field about 2.5 hours after injecting the radiopharmaceutical comprising $^{99m}$Tc.

35. A method for performing a parathyroidectomy to remove a parathyroid adenoma positioned in the chest comprising locating the parathyroid adenoma according to the method of claim 29 and excising the parathyroid adenoma.

36. A method according to claim 35 further comprising verifying that the excised tissue is hyperactive parathyroid tissue by determining the radioactivity of the excised tissue wherein excised tissue having radioactivity of 20% or greater than radioactivity measured in the operative field after excision of the tissue is deemed to be hyperactive parathyroid tissue.

37. A method for performing a parathyroidectomy according to claim 29 wherein the step of administering the radiopharmaceutical to the patient constitutes administering a second dose of the radiopharmaceutical to the patient, the method further comprising administering a first dose of the radiopharmaceutical to the patient, and performing a gamma surface mapping using a gamma detection device about 15 minutes after the first dose of the radiopharmaceutical is administered to the patient, the gamma surface mapping occurring before the second dose of the radiopharmaceutical is administered to the patient.

* * * * *